US007967860B1

(12) United States Patent
Gaskill

(10) Patent No.: US 7,967,860 B1
(45) Date of Patent: *Jun. 28, 2011

(54) PROSTHETIC BREAST FORM

(76) Inventor: Janis Twiddy Gaskill, New Bern, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/589,616

(22) Filed: Oct. 26, 2009

Related U.S. Application Data

(63) Continuation of application No. 11/598,359, filed on Nov. 13, 2006, now Pat. No. 7,628,811.

(51) Int. Cl.
A61F 2/52 (2006.01)
A61F 2/12 (2006.01)
(52) U.S. Cl. ................................. 623/7; 623/8
(58) Field of Classification Search .................. 623/7, 8
See application file for complete search history.

(56) References Cited

U.S. PATENT DOCUMENTS

| | | |
|---|---|---|
| 814,181 A | 3/1906 | Wolfe |
| 2,108,205 A | 2/1938 | Martin |
| 2,482,297 A | 9/1949 | Silverman |
| 2,580,264 A | 12/1951 | Wright et al. |
| 2,651,783 A | 9/1953 | Wright et al. |
| 2,867,818 A | 1/1959 | Creamer |
| 3,304,558 A | 2/1967 | Mann |
| 3,401,407 A | 9/1968 | Pittman |
| 3,619,810 A | 11/1971 | Mann |
| 3,641,592 A | 2/1972 | Den Bleyker |
| 3,795,921 A | 3/1974 | Zucker |
| 3,845,507 A | 11/1974 | Kirby et al. |
| 4,023,575 A | 5/1977 | Nixon |
| 4,071,914 A | 2/1978 | Silverman |
| 4,100,621 A | 7/1978 | Ettipio |
| 4,363,144 A | 12/1982 | Goad |
| 4,828,559 A | 5/1989 | Greenberg |
| 5,066,302 A | 11/1991 | Rice |
| 5,133,752 A | 7/1992 | Mandelkern |
| 5,158,541 A | 10/1992 | McCurley |
| 5,171,269 A | 12/1992 | Bark |
| 5,458,635 A | 10/1995 | Berman |
| 5,534,023 A | 7/1996 | Henley |
| 5,961,552 A | 10/1999 | Iversen et al. |
| 6,316,522 B1 | 11/2001 | Loomis et al. |
| 6,398,810 B1 | 6/2002 | Surprise |
| 6,544,287 B1 | 4/2003 | Johnson et al. |
| 6,623,523 B2 * | 9/2003 | Weber-Unger et al. ........... 623/7 |

OTHER PUBLICATIONS

Leisure—Post—Surgery, Trulife (Camp) breast form product literature. Date unknown.
Bosom Buddy Breast Forms product insert, B&B Company, Inc., Date unknown.
"Still You" breast form product literature, Date unknown.

(Continued)

*Primary Examiner* — David Isabella
*Assistant Examiner* — Yashita Sharma
(74) *Attorney, Agent, or Firm* — Miller Patent Services; Jerry A. Miller

(57) ABSTRACT

A prosthetic breast form that is worn external to the human body to simulate a missing breast or portion thereof has a fabric pouch that defines an outer shape that approximates a breast shape or portion thereof, and that further defines an inner compartment; and a filler disposed within the inner compartment, the filler comprising a free flowing blend of clustered fiber filler, filler beads and weighting beads that are intermingled, where the weight of the filler is between approximately 1.25 ounces and 40 ounces. This abstract is not to be considered limiting, since other embodiments may deviate from the features described in this abstract.

24 Claims, 1 Drawing Sheet

OTHER PUBLICATIONS

"Leading Lady" product literature for cotton covered breast prosthesis, Leading Lady, Beachwood, OH, Date unknown.

Trulife Naturealwear Model 611, Tri-Leisure Form, Jackson, MI, product literature, Date unknown.

* cited by examiner

PROSTHETIC BREAST FORM

CROSS REFERENCE TO RELATED DOCUMENTS

This application is a continuation of U.S. patent application Ser. No. 11/598,359 filed Nov. 13, 2006 now U.S. Pat. No. 7,628,811 to Janis Gaskill, which is hereby incorporated in its entirety by reference.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Each year, many thousands of women undergo mastectomy surgery. Such surgery can present serious trauma, both physical and emotional, following such surgery. While some women elect to have reconstructive surgery following a mastectomy, others choose not to. Those who choose not to undergo reconstructive surgery, generally still wish to have a physical appearance that resembles their pre-surgery appearance. Additionally, restoration of a pre-surgical feel is usually beneficial in overcoming both physical imbalance and emotional trauma associated with loss of a breast.

Breast forms are prostheses worn externally within the cup of a brassiere to simulate the lost breast. Such prosthetic breast forms have been made from various materials and are designed to either fit within fitted post-mastectomy brassieres which have included a stitched pocket or other means to hold the form in place, or within a conventional brassiere.

Breast forms are traditionally difficult to properly size and fit and suffer from numerous disadvantages. Often, such forms move and reshape during use resulting in an unnatural look. Some breast forms are unrealistic in feel, appearance, or movement. Some breast forms, particularly silicon or liquid filled breast forms are hot and often too heavy resulting in trapped perspiration and discomfort—sometimes sticking to or otherwise irritating the chest wall.

It has been found to be important, not only for self esteem and visual appeal, for a post-mastectomy patient to wear a breast form, but there is evidence that failure to compensate for the lost breast tissue can cause some women to develop spinal misalignment and chronic back pain as a result of failure to compensate for the loss of symmetry associated with loss of a natural breast.

Many prosthetic breast forms are available commercially, but all known devices suffer from various shortcomings such as being too hard, too heavy, too light, too rigid, too floppy, too hot to wear, unstable, costly, or unnatural in appearance and/or feel. Some such forms suffer from bunching or settling of the filling that requires frequent adjustment by the wearer, which may be both annoying and embarrassing.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

Figure 1:
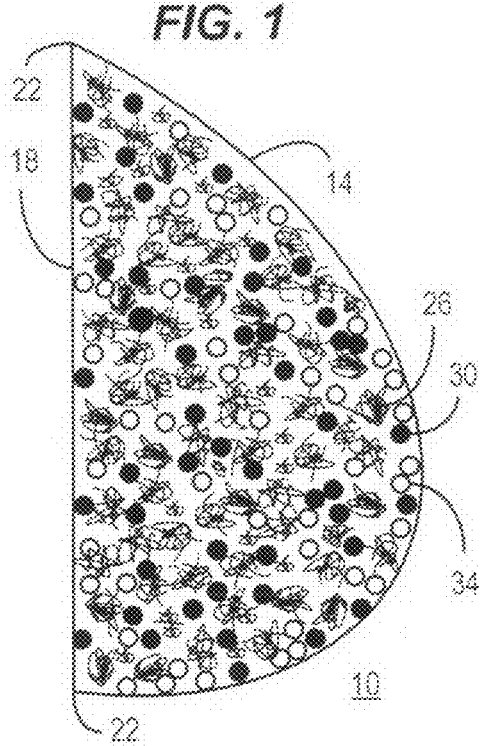
FIG. 1 depicts a side cutaway view of an illustrative embodiment of a prosthetic breast form consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

The term "clustered fiber fill", and similar terms, are used to describe fiber fill products that are produced as small clustered bodies of fiber threads. Such clustered fiber fill is readily available from sewing suppliers and is made up of small clusters (perhaps averaging approximately ⅛" to ½" or so in diameter when uncompressed (but embodiments consistent with the present invention are not limited to such cluster sizes). Visually, commercial embodiments such clustered polyester fiber fillers appear to be several strands of polyester that are curled or balled up and released to produce small ball-like structures of polyester fibers of varying diameters.

They appear to cling to each other and interlock somewhat to produce a very soft and airy filler product. The clusters appear to act as small interlocked three dimensional springs of very low spring coefficient. While polyester clustered fiber fill is currently preferred, similar products made of other materials than polyester may also be suitable.

These clusters tend to cling together and act like small three dimensional springs with very low spring coefficient. They are highly resilient and tend to return to an uncompressed state (perhaps of different form) after being compressed, i.e., they readily deform but spring outward when not under compressive forces. This type of fiber filler is light and airy and contributes to the natural feel of the prosthetic. Suitable polyester cluster fiber fill is available commercially from the Wal-Mart retail outlet as Cluster Stuff™ brand cluster fiber fill which is manufactured by Carpenter Company of 302 Highland Drive, Taylor, Tex. 76574 (a company based in Richmond, Va.). This material is used in embodiments consistent with the present invention to give the prosthetic bounce and softness as well as providing other desirable properties as will be discussed.

The term "bead", in some usage, often refers to an object that is spherical or approximately so, but as used herein can be interpreted more broadly to encompass spherical shapes as well as oval shapes, faceted shapes, pellets, balls, granules, crushed materials, symmetrical or asymmetrical shaped particles or aggregates that function in the capacity used herein. For illustrative clarity, the beads are shown in the drawing are illustrated substantially larger than scale when compared with the clustered fiber fill. The beads used herein serve multiple purposes and can be roughly classified into two classes—beads used primarily as filler, and beads used primarily to add weigh (i.e., filler beads and weighting beads (of course, both types of beads provide a measure of both filler volume and weight). Such beads can vary in diameter greatly from perhaps ¼ mm to perhaps 5 or 6 mm or so should be suitable. Present embodiments utilize beads that range from about ½ mm to about 2 mm. However, larger or smaller beads may also be suitable depending upon their other properties. It is desirable that the beads be small enough so as not to be visible through the surface of the finished breast form and brassiere.

One preferred type of filler beads used in embodiments consistent with the present invention are expanded polyester beads such as Poly-Fil® micro beads made by Fairfield company of Danbury Conn. 06810. For reference, such filler is often supplied, one half cubic foot bags that weigh approximately 1¼ pounds. These beads appear to vary in size from roughly ½ mm to 2 or 3 mm in diameter with substantial variation, but the size is not critical as long as the filler beads are small enough so as not to produce large visible lumps in the finished product and are able to reposition suitably to assist in producing the natural feel desirable in a prosthetic breast form.

One preferred type of weighting beads used in embodiments consistent with the present invention are referred to as clear caviar beads (0.038 inch) beads made by Viking polymers, LLC, and available from Allstar Plastic Industries, Montreal, Quebec, Canada. Such beads are made of polyvinyl chloride (PVC) can be used as the sole weighting beads to produce relatively lighter weight breast forms, or can be used in conjunction with other weighting beads. A 60 cc cup of such beads weighs approximately 1.6 oz for reference. Hence, similar beads of similar size, weight, surface and static characteristics may perform similarly.

Another type of heavier weighting beads that can be used in conjunction with the above weighting beads (or alone or combined with other beads in certain embodiments) are 1.5-2 mm glass beads available as item number 98013 from CR's Crafts, Mountain One Inc., 109 5$^{th}$ Ave. West, Leland, Iowa 50453. Most of these beads, visually, appear to be on average very slightly larger than the clear caviar beads described above, and are approximately 2-3 times as heavy. For reference, a 60 cc cup of such beads weighs approximately 3.8 oz. Again, similar beads of similar size, weight, surface and static characteristics may perform similarly.

It is generally desirable for the weighting beads to have smooth and relatively hard outer shells with a color that does not show through the breast form (which of course also depends upon the characteristics of the cover properties of the breast form). These characteristics should not be considered limiting, however.

Embodiments consistent with the present invention relate to a breast prosthesis such as those that are receivable within the cup of a brassiere. Desirable qualities of such prosthesis are that it simulates the look, feel and natural movement of a woman's breast. The prosthetic breast form should also preferably be comfortable against the chest wall and resist trapping perspiration or wick such perspiration away to prevent discomfort and other problems associated with moisture trapped against human flesh. Further, such prosthetic breast form preferably readily conforms to the contours of the post-surgical chest wall.

Turning now to FIG. 1, this illustration depicts a side cutaway view of an illustrative embodiment of a prosthetic breast form 10 consistent with certain embodiments of the present invention. The breast form 10 is produced by providing a pouch or pocket-like structure that can be fabricated in many arrangements. In the illustrated embodiment of breast form 10, the pouch is defined by a front panel 14 that is sewn to a rear panel 18 along a peripheral seam 22.

The front panel 14 should preferably be a slippery and stretchy material such as woven nylon or nylon blend, such as Lycra™ brand or other "stretchy" fabric. One fabric that is presently preferred in certain embodiments is a 90% nylon 10% spandex knitted fabric blend such as that used with some commercially available breast form covers. Other embodiments may use other ratios of nylon to spandex, e.g., 80% nylon and 20% spandex. Other stretchy fabrics may also be used without limitation.

The rear panel 18 (or back panel) is preferably made of a natural fabric material such cotton, cotton broadcloth, linen, wool, CoolMax certified fabric from INVISTA (Invista Building, 4123 East 37th Street North, Wichita, Kans. 67220), cotton containing materials, cotton blends, muslin or other moisture and vapor transmitting material so as to provide a comfortable surface to contact the chest wall of the wearer. Additionally, such materials should have a characteristic that wicks moisture away from the chest wall so as not to produce an uncomfortable trapping of moisture. The fabric may be knitted, woven or non-woven fabric. In a currently preferred embodiment, the rear panel 18 is 100% cotton knit material such as that used in high quality T-shirts so as to have a degree of stretch while providing the moisture wicking and vapor penetrating characteristics desired for comfort. The front panel material is preferably beige or white in color, but could be provided in any suitable color as required for a particular desired application including varying shades of beige and brown to match skin tone.

Figure 2:
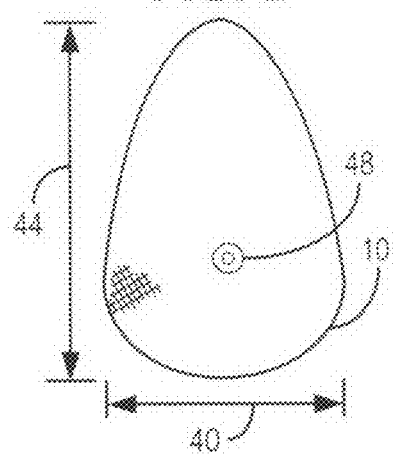
FIG. 2 is a front view of a tear drop shaped prosthetic breast form consistent with certain embodiments of the present invention.

In order to provide a suitable breast-like shape for the pouch, the front panel 14 can be pre-stretched over a suitable size ball or other form and sewn to a tear drop shaped rear panel 18 at seam 22 all around except for an area suitable for filling with the filler. This area can be later sealed either permanently or temporarily (e.g., with hook and loop fastener material such as Velcro™ brand). Using such a procedure produces a back panel 18 that will remain relatively flat while permitting the front panel 14 to adapt to most of the change in size resulting from the filling. While tear-drop shapes as illustrated in the front view of FIG. 2 are a desirable shape, the present invention is not to be constrained to such preferred shape, since any shape suitable for simulating a natural human breast (or partial natural breast) can be used.

In accordance with embodiments consistent with the present invention, the filler used is a mixture or blending of beads with fiber filler in such a manner that the beads and fiber filler intermingle. In particularly preferred embodiments, the pouch defined by front panel 14 and rear panel 18 is filled with a mixture of clustered fiber fill clusters 26, filler beads 30 and weighting beads 34. As shown in the drawing, the beads 30 and 34 and the clustered fiber fill 26 are illustrated schematically and are not to any scale. This mixture permits a degree of free flowing of the beads within the mixture, but the beads are somewhat constrained by the fiber filler that is interspersed throughout.

As discussed above, two separate types of beads are used in accordance with certain preferred embodiments herein. One type is used primarily to supply weight to the prosthetic breast form, while the other type is used primarily for fill. Such beads may be referred to respectively as weight beads or weighted beads 34, and filler beads 30 or fill beads or filling beads respectively. However, it is to be recognized that both types of beads, to varying degrees, serve both purposes. Additionally, in certain preferred embodiments, a mixture of two or more different weighting or filling beads can be used to enhance the weight and volume characteristics of the breast form. Moreover, experimentation with additional types of beads may result in a single type of bead that suitably provides both functions without departing from embodiments consistent with the present invention.

When mixed together in the breast form pouch, the fiber fill 26 provides restraint, softness, bounce and filling properties while trapping some of the beads 30 and 34 throughout the structure in the process. Further, the clustered fiber fill 26 conceals the shape of the beads 30 and 34 and fills between the beads 30 and 34 to maintain the softness of the breast form and preventing the prosthetic from having a sand-bag like feel. While clustered polyester fiber fill is preferred in embodiments of the present invention, unclustered fiber filler may possibly be substituted, but with less desirable resulting characteristics. In this blending of materials, the beads 30 and 34 are somewhat restrained by the fiber filler 26, but are still able to move about when touched or when the wearer moves about. While much of the weight is distributed throughout the breast form, many of the heavier weighting beads 34 will tend to migrate to the lowest point and permit the breast form 20 to sway and rearrange itself in a natural looking manner when the woman moves. The clustered fiber fill 26 provides a realistic springy feel when mixed with the beads 30 and 34 and the proportions of the beads 30 and 34 and clustered fiber fill 26 can be varied in order to provide the size, shape and weight suitable for matching the woman's natural breast.

The mixture of beads and fiber fill results in an intermingling of the beads with the fibers, as well as ability for the beads to move about among the other beads and the fiber fill. However, it should be noted that there is no separation (i.e., a wall, bag or cover, which separates beads from fiber fill. Hence, a free intermingling of the beads and fiber fill takes place and results in a natural feel and movement. Moreover, little to no undesirable bunching or excessive drooping takes place as would occur with only conventional fiber filler or arrangements of freely flowing beads alone. Furthermore, the present breast form does not have the problems of heat retention that causes sweating and discomfort associated with many existing breast forms.

The present breast form can be used adjacent the woman's chest wall comfortably, but can also be worn inside a breast form cover or can be placed in pocket of mastectomy brassiere. When placed adjacent the chest wall, a degree of massaging action also takes place as a result of movement by the wearer. Also, the form readily shapes to the contours of the chest wall caused by surgery. Additionally, the present breast form may be fabricated as a partial breast form without departing from embodiments consistent with the present invention—hence, the term "breast form" and shapes associated therewith should be broadly interpreted to encompass partial breast forms.

Thus, in accordance with certain embodiments consistent with the present invention, a prosthetic breast form that is worn external to the human body to simulate a missing breast is fabricated as a fabric pouch that defines an outer shape that approximates a full or partial breast shape, and that further defines an inner compartment. A filler material is disposed within the inner compartment, with the filler being made up of a free flowing blend of fiber filler and beads that are intermingled. The term free flowing is intended to mean that the beads are not confined to a separate compartment from the fiber filler and are free to comingle with the fiber filler. Depending upon the composition of the beads and the fiber in any particular embodiment, the beads may become suspended by or intertwined with the fiber or may adhere to the fiber due to static forces, but are free to move about if touched, squeezed, shaken, etc. The beads are not isolated from the fiber by a separate compartment.

The intermingling of the beads 30 and 34 with the fiber filler 26 permits movement of the beads 30 and 34, while simultaneously providing a degree of restraint against movement (i.e., simultaneously constrained but able to rearrange). The result is breast forms that is soft, suitably weighted and one that moves in a realistic manner along with the movement of the person wearing the prosthetic so as to accurately simulate the behavior of the missing breast or breasts.

Generally, such prosthetic breast forms come in standardized sizes from 1 to 15. In a relatively light weight embodiment, these sizes correspond roughly to the weight of PVC beads that would be used in a particular prosthetic. Thus, for a size 8, 8 ounces of PVC weighting beads 34 by weight can be used. This weighting contributes to a natural movement of the prosthetic. Approximately three times the volume of the PVC weighting beads 34 in polystyrene filler beads 30 is used. This amounts to approximately ½ ounce or so of the polystyrene beads filler beads 30 by weight. Finally, roughly about the volume of the desired finished prosthetic in uncompressed clustered fiber fill 30 is added. When these three constituents are mixed together inside the prosthetic, it creates a breast prosthetic that is cool, has natural movement and feel, and is comfortable to wear. As the user uses the prosthetic, some degree of massage action also takes place by the movement of the beads. If a heaver prosthetic is desired, heavier beads may be added or substituted. Moreover, the proportions described should be considered very approximate and a starting point for fitting a breast form to a particular individual. Such proportions can be varied substantially to personal preference and they can be adjusted to more closely match a remaining breast or to individualize the prosthetic.

As noted above, external breast prosthetics are sized according to a standardized numbering system ranging from 1 through 16. In accordance with certain embodiments consistent with the present invention, a suitable sized pouch is fabricated from a front panel 14 and a rear panel 18 to form a tear drop shape or other suitable shape. As another reference point for determination of how much of each filler component is placed inside the breast form, reference can be made to TABLE 1 below, that illustrates a very light weight breast form. This table assumes that the preferred PVC and polystyrene beads discussed above are used wherein the PVC beads are used for the weighting beads 34 while polystyrene beads are used for the filler beads 30. Additionally, the cluster fiber fill described above is used.

TABLE 1

| SIZE | WEIGHTING BEADS BY WEIGHT (oz) | FILLER BEADS BY WEIGHT (oz) | CLUSTER FIBER FILL VOLUME |
|---|---|---|---|
| 1 | 1.0 | 0.25 | Same as volume of beads |
| 2 | 2.0 | 0.50 | Same as volume of beads |
| 3 | 3.0 | 0.75 | Same as volume of beads |
| 4 | 4.0 | 1.00 | Same as volume of beads |
| 5 | 5.0 | 1.25 | Same as volume of beads |
| 6 | 6.0 | 1.50 | Same as volume of beads |
| 7 | 7.0 | 1.75 | Same as volume of beads |
| 8 | 8.0 | 2.00 | Same as volume of beads |
| 9 | 9.0 | 2.25 | Same as volume of beads |
| 10 | 10.0 | 2.50 | Same as volume of beads |
| 11 | 11.0 | 2.75 | Same as volume of beads |
| 12 | 12.0 | 3.00 | Same as volume of beads |
| 13 | 13.0 | 3.25 | Same as volume of beads |
| 14 | 14.0 | 3.50 | Same as volume of beads |
| 15 | 15.0 | 3.75 | Same as volume of beads |
| 16 | 16.0 | 4.00 | Same as volume of beads |

Generally speaking, TABLE 1 should be considered only a guide to providing the proportions of filler materials. The fiber fill volume is measured as uncompressed fiber filler, and could be further refined and defined by weight. Generally, a ratio of approximately four to one of filler beads to weighting beads provides a good result when combined with an approximately equal uncompressed volume of cluster fiber fill. However, a great deal of variability can be used in this mixture of filler components without departing from embodiments consistent with the present invention. For example, the heavier weight, the amount of weighting beads can be increased—for example by double the above amount or more. For lighter weight, the weighting beads can be halved or less. Increasing the volume of fiber fill will produce a firmer breast form and reduction of the volume of fiber fill will result in a less firm breast form.

In one example, a heavier weight prosthesis can be fabricated using double the above weight of weighting beads, half the above weighting of filler beads and half the volume of cluster fiber filler.

In another example, an extremely light weight prosthesis (e.g., as might be desired shortly after surgery, the weighting beads can be decreased by half or more, and the filler beads can be increased.

In certain embodiments, variations on the above formula for the constituents of the various filler components can be as illustrated in TABLE 2 below as compared with a commercially available line of breast forms as a reference standard. This table depicts formulae for light weight forms and for medium weight forms.

TABLE 2

| SIZE | REFERENCE STANDARD WEIGHT (oz) FOR COMPARISON | PVC WEIGHTING BEADS BY WEIGHT (oz) FOR LIGHT WEIGHT FORM | ADD APPROX. VOLUMES OF POLYSTYRINE AND CLUSTER FIBER FILLER FOR FINAL WEIGHT (oz) OF LIGHT FORM OF: | ADD GLASS WEIGHTING BEADS BY WEIGHT (oz) ADDED TO LIGHT WEIGHT FORM FOR MEDIUM WEIGHT FORM |
|---|---|---|---|---|
| 1 | 2.7 | 1.0 | 1.3 | 1.4 |
| 2 | 3.9 | 2.0 | 2.5 | 1.4 |
| 3 | 4.9 | 3.0 | 3.1 | 1.8 |
| 4 | 6.3 | 4.0 | 4.2 | 2.2 |
| 5 | 7.9 | 5.0 | 5.6 | 2.3 |
| 6 | 10.1 | 6.0 | 6.6 | 3.5 |
| 7 | 12.2 | 7.0 | 7.7 | 4.5 |
| 8 | 14.2 | 8.0 | 8.8 | 5.4 |
| 9 | 17.4 | 9.0 | 9.7 | 6.8 |
| 10 | 20.6 | 10.0 | 10.7 | 9.5 |
| 11 | 23.2 | 11.0 | 12.0 | 11.2 |
| 12 | 26.5 | 12.0 | 13.1 | 13.4 |
| 13 | 31.0 | 13.0 | 14.2 | 16.8 |
| 14 | 35.5 | 14.0 | 14.9 | 20.6 |
| 15 | 40.0 | 15.0 | 16.7 | 23.3 |

Again, the above formulae are preliminary approximates and should be considered as approximate starting points for experimentation to achieve a particular look, feel and behavior of any particular breast form prosthesis. By way of explanation of TABLE 2, if a size 6 breast form is to be fabricated, an appropriate size pouch is devised. If the form is to be a light weight form, it is filled with approximately 6.0 ounces of the PVC weighting beads plus equal volumes of polystyrene beads and cluster fiber filler to achieve a final weight of the form of 6.6 oz. It has been found easiest in manually filling the forms to blend approximately equal parts by volume of the polystyrene beads with the clustered fiber filler prior to adding it to the pouch. If a medium weight breast form is to be devised in a size 6, an additional 3.5 ounces of glass beads can be added. Of course, the above formulae can all be adjusted to achieve lighter or heaver breast forms as desired, hence these exact weights and volumes are not to be considered limiting.

Additionally, even lower weight breast forms can be fabricated for use immediately after surgery. These are referred to herein as after surgery fluff (ASF) forms. However, some amount of weight has been found desirable by most women even immediately post surgery. TABLE 3 below can be used to fabricate such a form.

TABLE 3

| SIZE | LIGHT WEIGHT (oz) FORM FINAL WEIGHT FOR COMPARISON | PVC WEIGHTING BEADS BY WEIGHT (oz) FOR ASF FORM | ADD APPROX. VOLUMES OF POLYSTYRINE AND CLUSTER FIBER FILLER FOR FINAL WEIGHT (oz) OF LIGHT FORM OF: |
|---|---|---|---|
| 1 | 1.3 | 0.5 | 0.6 |
| 2 | 2.5 | 1.0 | 1.2 |
| 3 | 3.1 | 1.3 | 1.5 |
| 4 | 4.2 | 1.9 | 2.1 |
| 5 | 5.6 | 2.5 | 2.8 |
| 6 | 6.6 | 3.0 | 3.3 |
| 7 | 7.7 | 3.5 | 3.8 |
| 8 | 8.8 | 4.0 | 4.4 |
| 9 | 9.7 | 4.5 | 4.9 |
| 10 | 10.7 | 5.0 | 5.5 |
| 11 | 12.0 | 5.5 | 6.2 |
| 12 | 13.1 | 6.0 | 6.7 |
| 13 | 14.2 | 6.5 | 7.1 |
| 14 | 14.9 | 7.0 | 7.8 |
| 15 | 16.7 | 7.5 | 8.3 |

In TABLE 3, the desired outcome is a breast form that is approximately ½ the total weight of the light weight form of TABLE 2 and the weight of PVC beads is approximately ½ the size number, more or less. Moreover, the weights provided in this table are approximate and can be adjusted to suit the user.

FIG. 2 is a front view of a tear drop shaped prosthetic breast form 10 consistent with certain embodiments of the present invention. While this shape is presently preferred, other shapes that simulate the shape of the female breast may be used. In this embodiment, dimension 40 ranges from approximately 3¼ inches for a size 1 to approximately 8½ inches for a size 16, varying approximately proportionally for sizes in between. Similarly, dimension 44 ranges from approximately 4½ inches for a size 1 to approximately 10 inches for a size 16, varying approximately proportionally for sizes in between. The widest dimension 40 appears approximately ⅔ of the way from top to bottom of the tear-drop shape. A filled depth of the breast form varies from about 1¼ inches for size 1 up to about 5 inches for size 16, again varying approximately proportionally for sizes in between. In some embodiments, it may be desirable to affix a prosthetic nipple and areola 48 to the front panel 14 to match a remaining breast more closely. Similarly, an areola and/or nipple can be imprinted upon the fabric to enhance the aesthetics. Most non-silicone external prosthetic breast forms do not incorporate such prosthetic nipple and areola 48, and hence, omission of such is presently preferred, but can be provided if desired.

Figure 3:
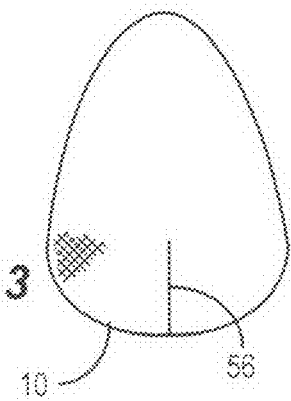
FIG. 3 is a front view of a prosthetic breast form using a one part front panel having a vertical dart at the bottom thereof consistent with certain embodiments of the present invention.

FIG. 3 depicts a front view of another embodiment of a prosthetic breast form 10 using a one part front panel having a vertically oriented dart 56 extending from the lower edge of the breast form 10 to approximately the broadest width area of the tear drop shape and extending from that point to the bottom thereof consistent with certain embodiments of the present invention. Providing such a dart serves to simulate a more lifted form in shape than the embodiment of FIG. 2. Much of the literature and patent documents relating to this technology describe various shapes used to simulate the human breast including the tear-drop shape described above as well as cone shapes and others. Any such shape is suitable for implementing embodiments of full and partial breast forms consistent with the present invention.

Figure 4:
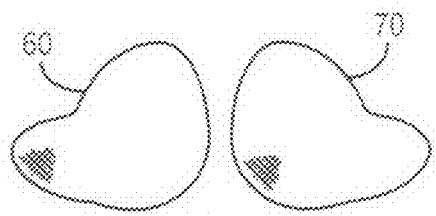
FIG. 4 is an illustration of an exemplary front view of a pair of left and right prosthetic breast forms consistent with certain embodiments of the present invention.

By way of further example, although it is preferred that a symmetrical form is used, left and right side breast forms are also preferred by some women. FIG. 4 is an illustration of an exemplary front view of a pair of left and right prosthetic breast forms 60 and 70 respectively consistent with certain embodiments of the present invention. In certain such breast forms as depicted, wings are provided on each side which extend under the right or left arms to form right or left sided forms. In other embodiments, a triangular shape or other suitable may be used with or without wings. Any such form used as a simulation or approximation of the human breast which can be defined by a pouch-like structure should be considered to be consistent with certain embodiments of the present invention. Hence, the illustrated shapes should be considered to be non-limiting examples of various breast form shapes that can be used in a manner consistent with embodiments of the present invention.

Figure 5:
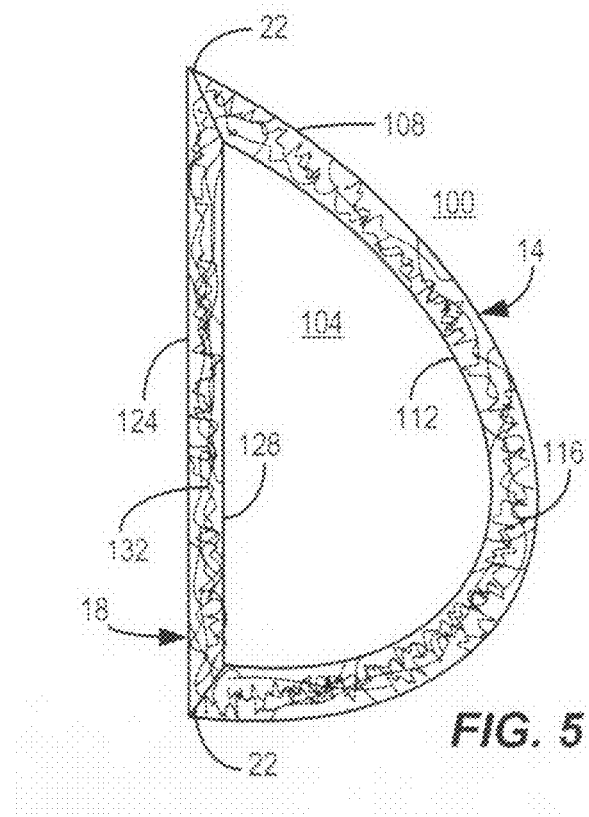
FIG. 5 depicts a partial cutaway side view of an illustrative embodiment of an exemplary prosthetic breast form having multi-layered front and rear panels (in which the filler has been omitted for illustrative clarity) consistent with certain embodiments of the present invention.

FIG. 5 depicts a partial cutaway side view of another embodiment of an exemplary prosthetic breast form having multi-layered front and rear panels (in which the filler has been omitted for illustrative clarity) consistent with certain embodiments of the present invention. In this embodiment, a breast form 100 is provided in a pouch-like configuration similar to that previously described in which an outer surface defines an approximation of a breast shape, and further defines an interior pouch 104. In this illustration, similar beads and fiber proportions as those provided previously can be used as a guideline, however, for illustrative clarity, the filler material has been omitted from this cutaway illustration. In this embodiment, a front panel 14 is fabricated from an exterior fabric panel 108 and an interior panel 112 that sandwiches a fiber 116 such as polyester quilting or other cushion layer therebetween in a somewhat quilt-like structure. Such sandwich structure can be made with various uncompressed thicknesses ranging from perhaps as thin as approximately ¹⁄₃₂ inch to perhaps as thick as approximately ½ inch. Preferably, the outer surface panel 108 is made of nylon or a nylon tricot blend or other suitable stretchy fabric that is slippery to the touch.

The rear panel 18 may similarly be made from a sandwich-like structure having an outer surface 124 panel and an inner surface panel 128 that captivates a fiber or other cushion-like layer 132, similarly such as polyester quilting filler. The thickness can run along a similar range as that of the front panel. The rearmost panel 124 should have characteristics similar to those described in connection with panel 18 of FIG. 1. The front and rear panels 14 and 18 are sewn together about the periphery in the same manner as that of breast form 10 at seam 22 and is similarly filled.

In another embodiment, the pouch can be devised as a one part bag-like knitted nylon pouch resembling a segment of a woman's nylon hose. If desired, the rear portion of the pouch can be lined on the exterior with a natural material such as cotton to achieve the coolness desired for contact with the chest wall.

In considering the embodiments shown in FIG. 1 and FIG. 5, it is understood that a hybrid design is also contemplated. In such design, a single layer front or rear panel 14 or 18 can be combined with a sandwiched structure rear or front panel 18 or 14 respectively without departing from embodiments consistent with the present invention. It is further understood that the present embodiments contemplate a fiber filler combined with beads in a manner such that the two types of fillers are intermingled with each other. One, two, three or more types of beads may be found to provide the most realistic look and feel of any given prosthetic and may be adjusted in many ways, including proportions of each component used, to achieve a matching breast form to match the infinite variations in human breasts. Additionally, the disclosure and claiming of the present components does not preclude the use of other or additional components. Although cluster fiber fill is the preferred fiber, other substitute fiber fill products may be used or subsequently devised without departing from embodiments consistent with the present invention.

Thus, a prosthetic breast form that is worn external to the human body to simulate a missing breast, the prosthetic breast form has a fabric pouch that defines an outer shape that approximates a breast shape, and that further defines an inner compartment. A filler disposed within the inner compartment, the filler comprising a free flowing blend of fiber filler and beads that are intermingled. The fiber filler can be clustered fiber filler such as clustered polyester fiber filler. The beads can be of various types that provide weight and volume as a primary function. The weighted beads can include glass beads or PVC beads, and filler beads can be used that include polystyrene beads. The pouch includes a rear panel and a front panel, preferably with the rear panel being made of an absorbent fabric and the front panel being made of a stretchy fabric. The rear panel can define any suitable breast shape including a tear-drop shape. The pouch can be made up of a rear panel and a front panel and wherein at least one of the rear panel and the front panel has first and second fabric layers that sandwich a fiber fill layer.

In another embodiment, a prosthetic breast form that is worn external to the human body to simulate a missing breast, the prosthetic breast form has a fabric pouch that defines an outer shape that approximates a breast shape, and that further defines an inner compartment; and a filler disposed within the inner compartment, the filler comprising a free flowing blend of clustered fiber filler and beads, the beads comprising a plurality of weighting beads and a plurality of filler beads.

In another embodiment, a prosthetic breast form that is worn external to the human body to simulate a missing breast, the prosthetic breast form has a fabric pouch that defines an outer shape that approximates a breast shape, and that further defines an inner compartment, wherein the pouch comprises rear panel for contacting the chest surface of the user and a front panel, with the rear panel being made of an absorbent natural fabric and the front panel being made of a stretchy fabric. A filler is disposed within the inner compartment, the filler including a free flowing blend of clustered polyester fiber filler and beads, the beads comprising a plurality of weighting beads and a plurality of filler beads.

While certain illustrative embodiments have been described, it is evident that many alternatives, modifications, permutations and variations will become apparent to those skilled in the art in light of the foregoing description.

What is claimed is:

1. A prosthetic breast form that is worn external to the human body to simulate a missing breast or portion thereof, the prosthetic breast form comprising:
    a fabric pouch that defines an outer shape that approximates a breast shape or portion thereof, and that further defines an inner compartment; and
    a filler disposed within the inner compartment, the filler comprising a free flowing blend of clustered fiber filler, filler beads and weighting beads that are intermingled, where the weight of the filler is between approximately 1.25 ounces and 40 ounces.

2. The prosthetic breast form according to claim 1, wherein a weight of the weighting beads is approximately four times the weight of the filler beads.

3. The prosthetic breast form according to claim 2, wherein a weight of the filler beads is approximately the same as a weight of the clustered fiber filler.

4. The prosthetic breast form according to claim 1, wherein a weight of the weighting beads comprises less than half the weight of the breast form.

5. The prosthetic breast for according to claim 4, wherein the weighting beads comprise glass beads.

6. The prosthetic breast form according to claim 1, wherein the weighting beads have a weight between 1 and 38.3 ounces.

7. The prosthetic breast form according to claim 1, wherein the filler beads comprise expanded polystyrene beads.

8. The prosthetic breast form according to claim 1, wherein the pouch comprises rear panel and a front panel, with the rear panel being made of an absorbent fabric and the front panel being made of a stretchy fabric.

9. The prosthetic breast form according to claim 8, wherein the rear panel is either approximately tear-drop shaped or approximately triangular shaped.

10. The prosthetic breast form according to claim 1, wherein the pouch comprises a rear panel and a front panel and wherein at least one of the rear panel and the front panel comprises first and second fabric layers that sandwich a fiber fill layer.

11. The prosthetic breast form according to claim 1, wherein a volume of the clustered fiber filler is approximately the same as a volume of the filler beads.

12. A prosthetic breast form that is worn external to the human body to simulate a missing breast or portion thereof, the prosthetic breast form comprising:
    a fabric pouch that defines an outer shape that approximates a breast shape or portion thereof, and that further defines an inner compartment; and
    a filler disposed within the inner compartment, the filler comprising a free flowing blend of clustered fiber filler and beads, the beads comprising a plurality of weighting beads and a plurality of filler beads, and wherein a volume of the filler beads is approximately the same as a volume of the clustered fiber filler.

13. The prosthetic breast form according to claim 12, wherein a weight of the weighting beads is approximately four times the weight of the filler beads.

14. The prosthetic breast form according to claim 12, wherein a weight of the filler beads is approximately the same as a weight of the clustered fiber filler.

15. The prosthetic breast form according to claim 12, wherein the weighting beads have a weight between about 1 and 16 ounces.

16. The prosthetic breast form according to claim 12, wherein the filler beads comprise expanded polystyrene beads.

17. The prosthetic breast form according to claim 12, wherein the pouch comprises rear panel and a front panel, with the rear panel being made of an absorbent fabric and the front panel being made of a stretchy fabric.

18. The prosthetic breast form according to claim 17, wherein the rear panel is either approximately tear-drop shaped or approximately triangular shaped.

19. The prosthetic breast form according to claim 12, wherein the pouch comprises a rear panel and a front panel and wherein at least one of the rear panel and the front panel comprises first and second fabric layers that sandwich a fiber fill layer.

20. A prosthetic breast form that is worn external to the human body to simulate a missing breast or portion thereof, the prosthetic breast form comprising:
   a fabric pouch that defines an outer shape that approximates a breast shape or portion thereof, and that further defines an inner compartment, wherein the pouch comprises rear panel for contacting the chest surface of the user and a front panel, with the rear panel being made of an absorbent natural fabric and the front panel being made of a stretchy fabric, and where the rear panel is either approximately tear drop or triangular shaped; and
   a filler disposed within the inner compartment, the filler comprising a free flowing blend of clustered polyester fiber filler and beads, the beads comprising a plurality of weighting beads and a plurality of filler beads, and where a total weight of the breast form is between approximately 1 and 40 ounces.

21. A prosthetic breast form that is worn external to the human body to simulate a missing breast or portion thereof, the prosthetic breast form comprising:
   a fabric pouch that defines an outer shape that approximates a breast shape or portion thereof, and that further defines an inner compartment;
   where the fabric pouch has vapor penetrating characteristics;
   and a filler disposed within the inner compartment, the filler comprising a free flowing blend of filler beads and weighting beads that are intermingled, where the filler beads are different from the weighting beads, and where a proportion and amount of weighting beads and filler beads is selected to produce a predetermined volume and weight of the breast form, and where the proportion of weighting beads to filler beads is between approximately 16:1 and approximately 0.77:1.

22. The prosthetic breast for according to claim 21, wherein the weighting beads comprise at least one of glass beads and PVC beads.

23. The prosthetic breast form according to claim 21, wherein at least a portion of the filler beads comprise expanded polystyrene beads.

24. The prosthetic breast form according to claim 21, wherein the pouch comprises a rear panel and a front panel and wherein at least one of the rear panel and the front panel comprises a cushion-like layer.

* * * * *